United States Patent [19]
Hsiao

[11] Patent Number: 5,820,562
[45] Date of Patent: Oct. 13, 1998

[54] SKIN ALLERGY TEST DEVICE HAVING STEP-SHAPED PUNCTURES

[76] Inventor: Ray-Ling Hsiao, 4F, No. 12, Aly. 15, Ln. 175, Sec. 2, HoPing E. Rd., Taipei, Taiwan

[21] Appl. No.: 964,982

[22] Filed: Nov. 5, 1997

[51] Int. Cl.$^6$ .................................................. A61B 5/00
[52] U.S. Cl. ............................................................ 600/556
[58] Field of Search .............................. 600/556; 604/46, 604/47

[56] References Cited

U.S. PATENT DOCUMENTS

| | | | |
|---|---|---|---|
| 3,688,764 | 9/1972 | Reed | 600/556 |
| 4,237,906 | 12/1980 | Havstad et al. | 604/47 |
| 4,453,926 | 6/1984 | Galy | 604/47 |
| 5,551,441 | 9/1996 | Pitesky | 600/556 |
| 5,735,288 | 4/1998 | Fishman | 600/556 |
| 5,746,700 | 5/1998 | Hsiao | 600/556 |
| 5,749,836 | 5/1998 | Hsiao | 600/566 |

*Primary Examiner*—Max Hindenberg
*Assistant Examiner*—Charles Marmor, II
*Attorney, Agent, or Firm*—W. Wayne Liauh

[57] ABSTRACT

A skin allergy test device includes a skin allergy test bar and an antigen container. The skin allergy test bar includes a finger grip, an integral cover having a sealing plug portion, an elongated stem extending therefrom, and a plurality of step-shaped punctures, wherein each puncture has a flat step to act as a stop and an integral sharp tip projecting out from the flat step. Each sharp tip has a length shorter than the thickness of the epidermis layer of the skin of human beings such that each puncture will not penetrate the epidermis layer of the skin of human beings due to the flat step of the punctures acting as a stop during a skin allergy test. The container has an inner compartment for storing antigen solution, a top opening for receiving the sealing plug of the skin allergy test bar securely, and a middle opening intercommunicating the inner compartment and top opening. The middle opening has a diameter slightly greater than which of the elongated stem of the skin allergy test bar and is formed with an inner coarse surface for wiping off the antigen solution left on the surface of elongated stem.

6 Claims, 5 Drawing Sheets

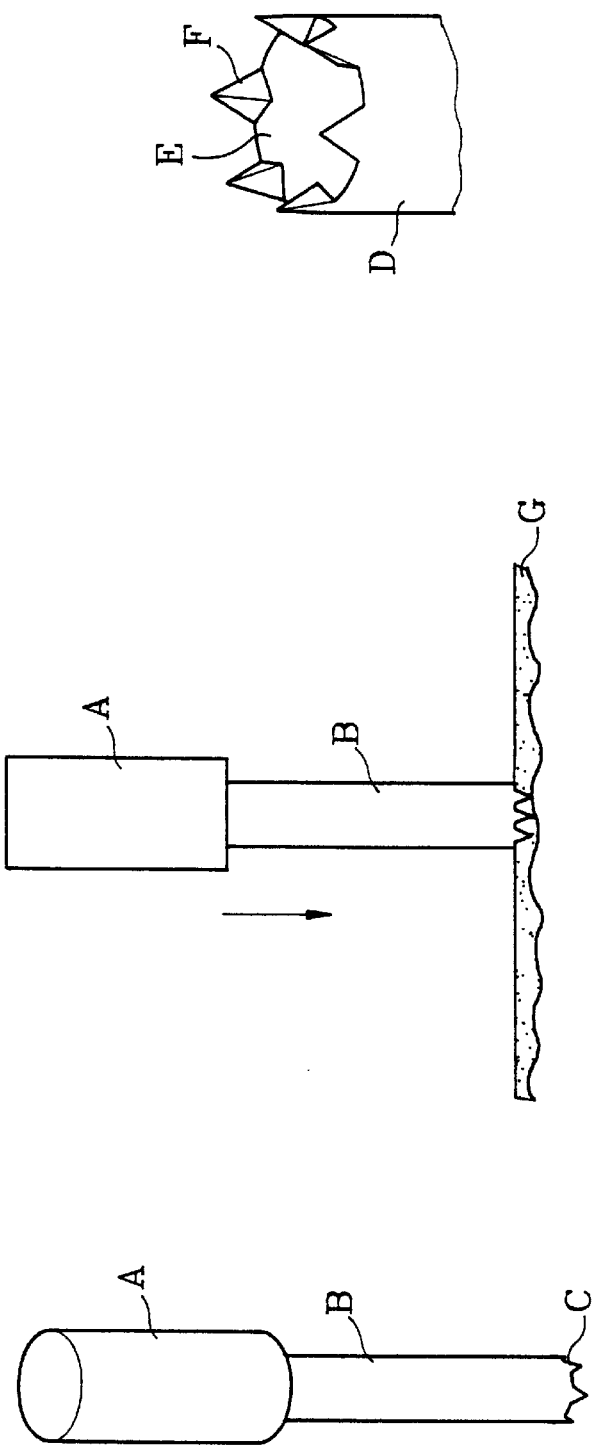

SKIN ALLERGY TEST DEVICE HAVING STEP-SHAPED PUNCTURES

FIELD OF THE INVENTION

The present invention relates to a skin allergy test device which includes at least a skin allergy test bar and an antigen container. The improved features of the skin allergy test bar in accordance with the present invention include some step-shaped punctures by which a limited penetration can be made for facilitating a skin allergy test.

BACKGROUND OF THE INVENTION

For a skin allergy test, the allergic test conducted by a skin test device of puncture type is one of the most common ways at present. One example of such a device, as shown in FIG. 1, comprises a finger grip (A), an elongated stem (B) extending therefrom, and a plurality of punctures (C) attached to the end of the elongated stem (B). In use, the test device, like other skin allergy test bars of prior type, is employed to press in contact with a skin portion of a patient, such as the forearm skin, and then has its punctures brought into the epidermis layer (G) of the skin of a patient. A properly performed skin allergy test will leave a visible scarification which corresponds to the punctures thereof. In the test process, a certain amount of antigen liquid loading onto punctures by the capillary phenomenon may be transferred to the test site of the epidermis layer of the skin of the patient. Finally, the test result may be properly interpreted about 20 minutes after the specific antigen liquid has been provided.

Although various conventional skin allergy test bars of puncture type have provided the practitioners or technicians in the art with a convenient way in performing a skin allergy test, yet none of the conventional test devices can be performed to obtain a correct and reproducible test result by a person with ordinary skill in the art, since the skin allergy test performed by any skin allergy test bars of puncture type are required to meet the following test conditions in order to obtain an accurate interpretation for the test result.

(1) the punctures of a skin allergic prick test device are not allowed to penetrate past the epidermis layer of the skin of a patient during the skin allergy test, as indicated in Allergic Principles And Practice, 3rd edition, Page 423–425, by Elliott et al.; and (2) the skin allergy test is required to be easily used by anyone with ordinary skill, therefore making the test data reproducible and assuring the test reliability.

However, the epidermis layer of a human being is extremely thin, it is therefore very likely for the epidermis layer of the skin to be penetrated by the punctures of the test devices in the test process. As a result, the device as shown in FIGS. 1–3, should be operated by a practitioner or technician very skillful in the art in order to guarantee its reliability.

A disclosed skin allergy test bar, U.S. Pat. No. 4,237,906 to Havstad et al., as shown in FIG. 3, describes an applicator or skin puncture test device having the flat end surface (E) which is provided at the end of the elongated stem (D), and a plurality of pointed projections (F) which are attached to the flat end surface (E), where the flat end surface (E) may act as a stop to limit further penetration of the punctures in the test process.

Although the flat end surface (E) can act as a stop to limit the depth of penetration, it is very difficult for such an applicator to be in the way that its punctures have the length of between about 0.1 mm to about 0.5 mm, so as to avoid excessive penetration of the punctures. Even though such a manufacturing difficulty may be overcome, the punctures thereof will be very short and incapable of carrying sufficient antigen liquid, by its capillarity, so as to conduct the test.

U.S. patents relating to the introduction of skin allergy test also include Maganias U.S. Pat. No. 4,802,493, Pitesky U.S. Pat. No. 5,551,441, 5,538,134, Hein et al. U.S. Pat. No. 3,556,080, Brennan et al. U.S. Pat. No. 4,607,632.

SUMMARY OF THE INVENTION

The primary objective of the present invention is to provide an improved skin allergy test bar, which comprises a finger grip, an integral cover having a sealing plug, an elongated stem extending therefrom, and a plurality of step-shaped punctures; wherein each step-shaped puncture is formed with a flat step to act as a stop and an integral sharp tip projecting out from the flat step. Each sharp tip has a length shorter than the thickness of the epidermis layer of the skin of human beings such that each puncture will not penetrate the epidermis layer of the skin of human beings due to the flat step of the punctures acting as a stop during a skin allergy test.

The skin allergy test bar can further have at least a raised portion formed on the end of the elongated stem to act as a stop. The raised portion has the same height as which of the flat step of the puncture such that a flat and reliable stopping mechanism can therefore be formed by means of the raised portion and the flat steps of the punctures. Thus a skin allergy test can be easily processed by anyone with ordinary skill, and the accuracy and reproducibility of the test result can be assured.

Another objective of the present invention is to provide a skin allergy test device which includes at least a skin allergy test bar and an antigen container. The antigen container comprises an inner compartment for storing antigen solution, a top opening for receiving the sealing plug of the skin allergy test bar, and a middle opening intercommunicating the inner compartment and top opening. The top opening is capable to receive the sealing plug of the skin allergy test bar securely so as to prevent the antigen solution stored within the container from being contaminated or spilled. The middle opening has a diameter slightly greater than which of the elongated stem of the skin allergy test bar and is formed with an inner coarse surface acting as a tongue tip for wiping off the antigen solution left on the surface of elongated stem.

BRIEF DESCRIPTION OF THE DRAWINGS

The foregoing features of the present invention may be more fully understood from the following detailed description, read in conjunction with the accompanying drawings, wherein:

FIG. 1 shows a conventional skin allergy test device of prior art.

FIG. 2 is a schematic diagram showing how a skin allergy test bar of prior art is to be operated.

FIG. 3 shows another skin allergy test bar of prior art in which the punctures are formed at a flat end surface which acts as a stop.

DETAILED DESCRIPTION OF THE PREFERRED EMBODIMENTS

Figure 4:
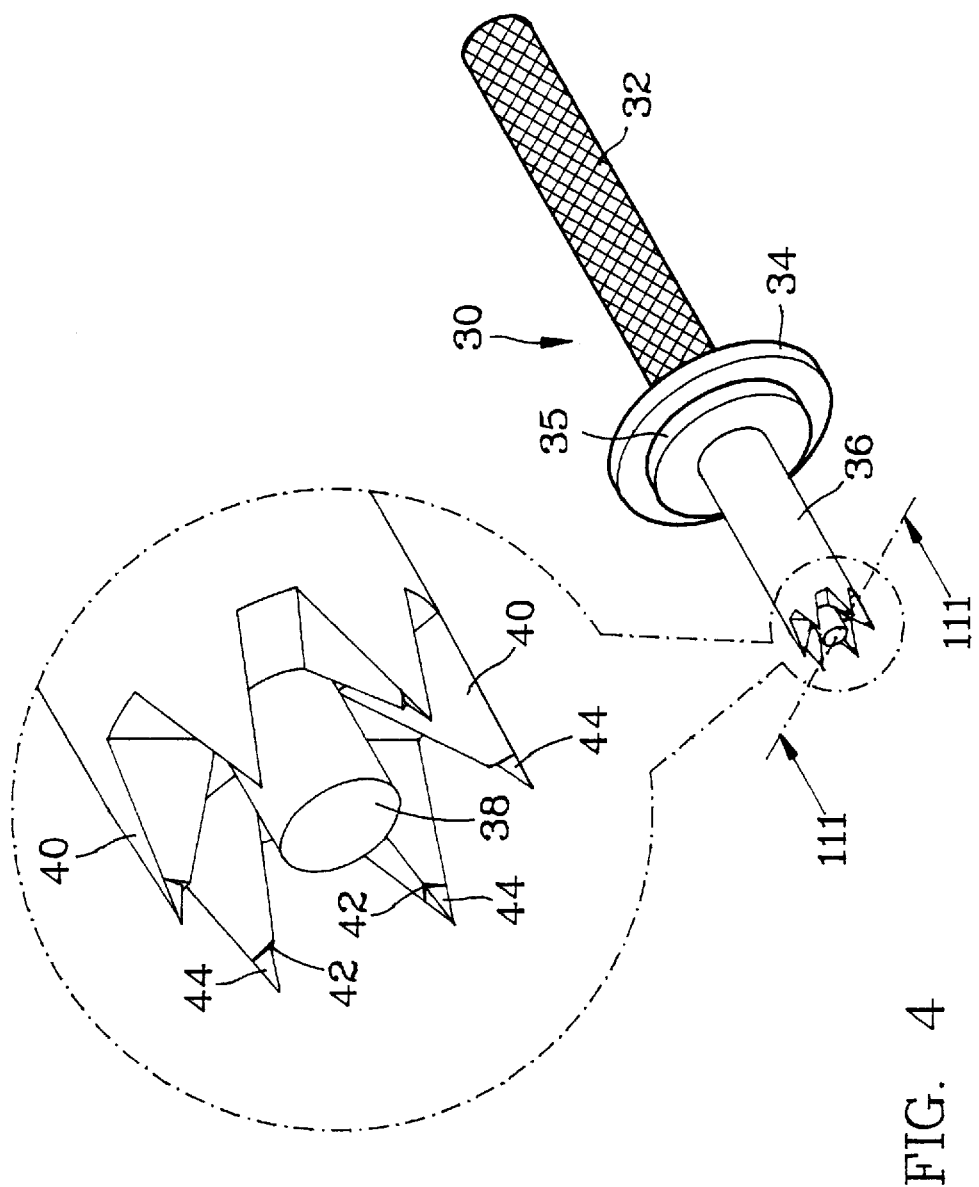
FIG. 4 is a perspective view of a skin allergy test bar of the present invention.

Please refer to FIG. 4, it is the perspective view of a skin allergy test bar 30 of the present invention. As shown in the figure, the skin allergy test bar 30 comprises a finger grip 32 to be held by fingers; an integral cover 34 provided at the bottom of the finger grip 32, which has a sealing plug 35 portion adaptful to the top opening 58 of an antigen container 50 (see FIG. 7); and an elongated stem 36 extending downward from the sealing plug 35. The sealing plug 35 has a diameter greater than which of the stem 36 but less than which of the cover 34. The stem 36 is elongated and defines a longitudinal axis thereof. A plurality of step-shaped punctures 40 are provided at the end of the elongated stem 36, which extend along a direction substantially parallel to the longitudinal axis of the elongated stem 36. Each step-shaped puncture 40 is formed with a flat step 42 lying on a surface substantially vertical to the longitudinal axis of the elongated stem 36, whereas each step-shaped puncture 40 is also formed with a sharp tip 44 extends from the flat step 42 along a direction substantially parallel to the longitudinal axis. The flat step 42 is spaced apart from the root of the puncture 40 with a length of about 3~5 mm preferably. The flat step 42 and the sharp tip 44 are integrally formed and thus substantially is less than the thickness of the epidermis layer of the skin of human beings, which is preferably between 0.1 mm~0.5 mm. However, it is noted that the length of the sharp tip 44 may also be more than 0.5 mm or less than 0.1 mm, as it may be an obvious design choice for any person skilled in the art. In addition to the above mentioned step-shaped punctures 40, at least a raised portion 38 can also be provided at the end of the elongated stem 36 to act as a stop. The raised portion 38 has the same height (preferably 3~5 mm) as which of the flat step 42 of the puncture 40 such that a flat and reliable stopping mechanism can therefore be formed by means of the raised portion 38 and the flat steps 42 of the punctures 40, which is the most important guideline that a technician or practitioner is required to obey in order to obtain an accurate interpretation of the test result and to make the test data reproducible and assure the test reliability. Thus a skin allergy test can be easily processed by anyone with ordinary skill, and the accuracy and reproducibility of the test result can be assured.

Figure 5:
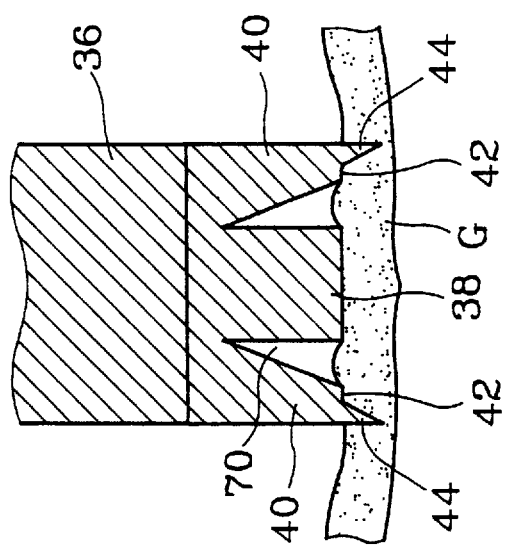
FIG. 5 is a sectional enlarged view of FIG. 4 taken along line 111—111, showing the operating method of the skin allergy test bar of the present invention.

When using the skin allergy test bar 30 of the present invention, firstly the punctures 40 of the skin allergy test bar 30 are dipped with antigen solution. The length of the punctures 40 (approximately 3~5 mm) are relatively long, in comparison with the sharp tips 44 of 0.1~0.5 mm only, such that an adequate amount of antigen solution 70 can be carried among the punctures 40 and raised portion 38 by capillary phenomenon, as shown in FIG. 5. The skin allergy test bar 30 is then applied to the skin of a human being, having the sharp tips 44 sticking into the epidermis layer (G) of skin. In the mean time, the flat steps 42 of the punctures 40 and the raised portion 38 act as a stopping mechanism to limit excessive penetration of the punctures 40. Therefore the punctures 40 can be prevented from penetrating through the epidermis layer (G) of skin, and an accurate, reliable and reproducible test result can be acquired. Because the opposite surfaces between the punctures 30 and the raised portion 38 are manufactured to be smooth and slippery, the antigen solution 70 carried therebetween will apply to the relatively coarse skin surface easily due to the capillarity and gravity effect when the sharp tips 44 stick into the epidermis layer (G) of skin.

Figure 6:
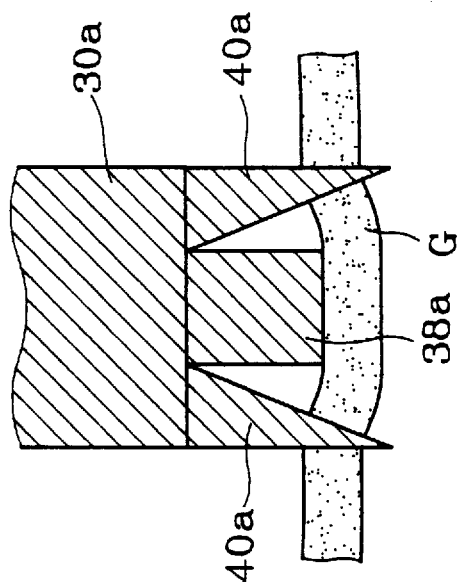
FIG. 6 is a sectional view similar to FIG. 5, wherein the punctures of the skin allergy test bar are not formed with flat steps and sharp tips.

The implement of the flat steps 42 is essential in the present invention. It is because that when a skin allergy test bar 30a without flat steps formed on the punctures 40a is applied to the skin of a human being, the upper surface of the skin will be pressed down by the raised portion 38a, as shown in FIG. 6, which consequently results in a possibility that the punctures 40a may still have a small chance to penetrate through the epidermis layer (G) due to the deformation of skin surface, especially when the punctures 40a are not sticking into the skin in a vertical angle or the test bar 30a is not operated by a skilled technician. Although such a possibility is low and may not happen frequently, it is still recommended to make improvement of the "non-step-shaped" punctures 40a shown in FIG. 6 so as to definitely ensure the reliability and reproducibility of the skin allergy testing result. By forming a flat step 42 at each puncture 40 of the skin allergy test bar 30 in the same height level as which of the raised portion 38 as shown in FIG. 4 and FIG. 5, each puncture 40 can be provided with its own stopping mechanism (i.e., the flat step 42). Thus the possibility of the epidermis layer (G) being over-penetrated by punctures 40 can be eliminated absolutely, and the reliability, accuracy and reproducibility of the test result can also be assured.

Figure 8:
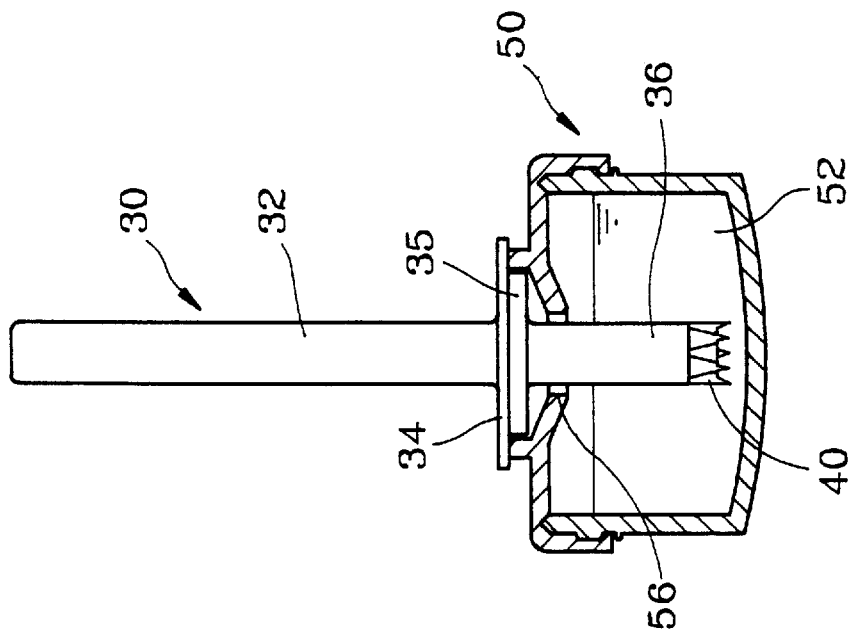
FIG. 8 shows the antigen container of FIG. 7 where a skin allergy test bar is brought to mate therewith.
Figure 7:
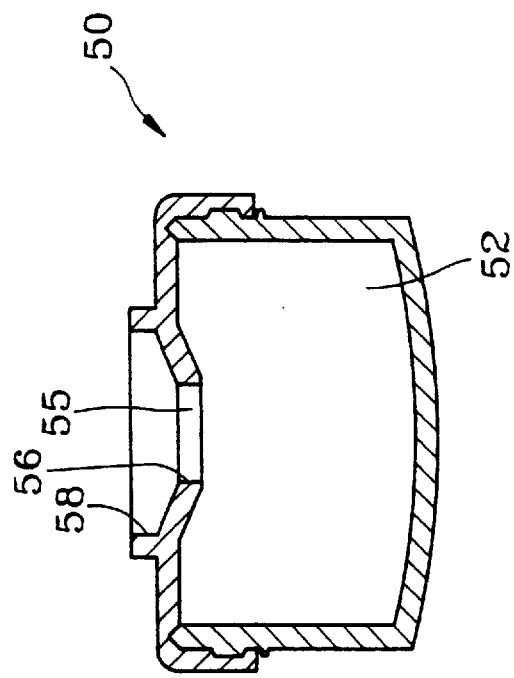
FIG. 7 shows an antigen container according to the present invention.

Referring next to FIG. 7 and FIG. 8, the skin allergy test bar 30 of the present invention may be put into an antigen container 50 to act as a top cover of the antigen container 50 for facilitating the operation of a skin allergy test. The antigen container 50 has an inner compartment 52 for storing antigen solution, a top opening 58 for receiving a skin allergy test bar 30, and a middle opening 55 intercommunicating the inner compartment 52 and top opening 58. The top opening 58 is capable to receive the sealing plug 35 of the skin allergy test bar 30 securely so as to prevent the antigen solution stored within the container 50 from being contaminated or spilled. The middle opening 55 has a diameter slightly greater than which of the elongated stem 36 of the skin allergy test bar 30 and is formed with an inner coarse surface 56 to act as a tongue tip for wiping off the antigen solution left on the surface of elongated stem 36. As shown in FIG. 7 and FIG. 8, when the skin allergy test bar 30 is mated with the container 50, the punctures 40 will be wetted by the antigen solution stored in the inner compartment 52 of the antigen container 50, such an aspect regarding the skin allergy test bar 30 will therefore facilitate the next skin allergy test. Also, as shown in the figures, we note that the sealing plug 35 of the cover 34 of the skin allergy test bar 30 is placed over the top opening 58 of the antigen container 50, such feature regarding the cover 34 will prevent foreign materials from entering the antigen container 50. The inner coarse surface 56 of the middle opening 55 of the antigen container 50 is essential in the present invention since the coarse surface 56 can act as a tongue tip to wipe the antigen solution left on the surface of elongated stem 36 back to the inner compartment 52, while leaving some small gaps on the coarse surface for air to pass through when the skin allergy test bar 30 is pulled out from the container 50.

Figure 9:
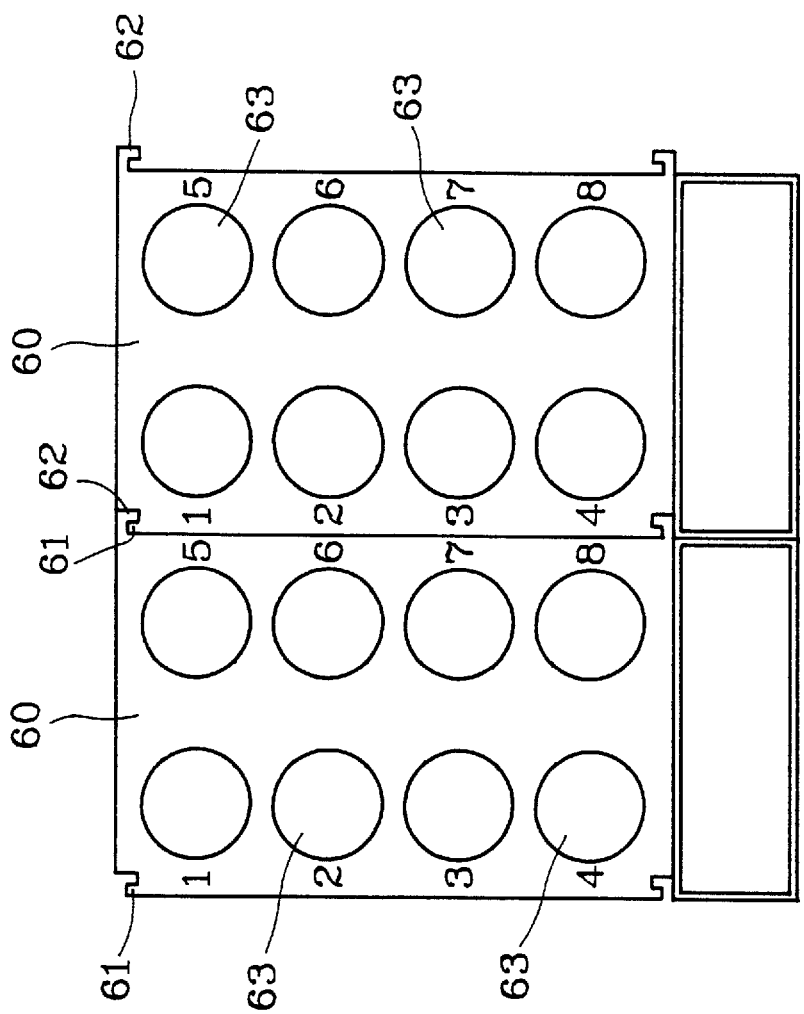
FIG. 9 is a top side view of a tray set according to the present invention.

Referring to FIG. 9, a tray 60 having a plurality of round holes 63 can also be employed for facilitating allergy tests. Each round hole 63 of the tray 60 is capable to hold an antigen container 50 of the present invention. Two opposite sides of the tray 60 are formed with a male connecting mechanism 61 and a female connecting mechanism 62 respectively. Therefore several trays 60 can be assembled one by one by means of the connecting mechanism 61,62 so as to facilitate allergy tests when a vast amount of tests using various kind of antigen solutions are needed.

Further, the present device is not only capable to be applied in a skin allergic test of sequential manner, as described in this disclosure, where each time only one skin test device, with a specific antigen liquid, is allowed to do the test; but also capable to be applied in a skin allergic test of simultaneous manner, as described in U.S. Pat. No. 3,556,080, issued in 1971 to Hein et al., where the present device (e.g., step-shaped punctures) can be provided at each leg of the disclosed multileg skin-testing device to assure its test reliability. In addition, the amount and location of the round holes 63 of the tray 60 shown in FIG. 9 can also be designed in such a manner that the tray 60 is capable for using with the multileg skin-testing device mentioned right above.

Although the description above contains many references to specific versions and aspects of the invention, this circumstance should not be construed as limiting the scope of the invention but as merely providing illustrations of some of the presently preferred embodiments of this invention. Therefore, the scope of this invention should be determined by the appended claims and their legal equivalents, rather than by the examples given in the descriptions above.

I claim:

1. A skin allergy test bar of the type which has a finger grip, an elongated stem extending from one end of the finger grip defining a longitudinal axis thereof, and a plurality of punctures provided at a distal end of said elongated stem, said punctures extending along a direction substantially parallel to the longitudinal axis of said elongated stem, the improvement comprising:

each said puncture being step-shaped and having a flat step lying on a surface substantially vertical to the longitudinal axis to act as a stop and an integral sharp tip extending from said flat step along a direction substantially parallel to said longitudinal axis, each said sharp tip having a length shorter than the thickness of the epidermis layer of the skin of human beings such that each puncture will not penetrate the epidermis layer of the skin of human beings due to said flat step of the punctures acting as a stop during a skin allergy test.

2. The skin allergy test bar of claim 1, wherein said sharp tip has a length between 0.1 mm and 0.5 mm.

3. The skin allergy test bar of claim 1, wherein the improvement further comprises:

the end of said elongated stem further having at least a raised portion to act as a stop, said raised portion having the same height as which of the flat step of the puncture.

4. The skin allergy test bar of claim 1, wherein the improvement further comprises: said skin allergy test bar further including an integral cover which has a sealing plug, said cover being located between said finger grip and the elongated stem while said sealing plug being located between the cover and the elongated stem, the sealing plug having a diameter greater than which of the stem but less than which of the cover.

5. A skin allergy test device comprising:

a skin allergy test bar having a finger grip, an elongated stem extending from one end of the finger grip defining a longitudinal axis thereof, a plurality of step-shaped punctures provided at a distal end of said elongated stem, and an integral cover which has a sealing plug, said cover being located between said finger grip and the elongated stem while said sealing plug being located between the cover and the elongated stem, the sealing plug having a diameter greater than which of the stem but less than which of the cover, said step-shaped punctures extending along a direction substantially parallel to the longitudinal axis of said elongated stem, each said step-shaped puncture having a flat step lying on a surface substantially vertical to the longitudinal axis to act as a stop and a sharp tip extending from said flat step along a direction substantially parallel to said longitudinal axis, each said sharp tip having a length shorter than the thickness of the epidermis layer of the skin of human beings; and an antigen container having an inner compartment for storing antigen solution, a top opening for receiving the sealing plug of the skin allergy test bar, and a middle opening intercommunicating said inner compartment and top opening, said top opening being capable to receive the sealing plug securely so as to prevent the antigen solution stored within the container from being contaminated, said middle opening having a diameter slightly greater than which of the elongated stem and being formed with an inner coarse surface for wiping off the antigen solution left on the surface of elongated stem.

6. The skin allergy test device of claim 5, wherein a distal end of said elongated stem of the skin allergy test bar further having at least a raised portion to act as a stop, said raised portion having the same height as which of the flat step of the puncture.

* * * * *